ized Patent [19]

United States Patent [19]

Kilty

[11] 4,207,210
[45] Jun. 10, 1980

[54] PROCESS FOR PREPARING AN ETHYLENE OXIDE CATALYST

[75] Inventor: Peter A. Kilty, Houston, Tex.

[73] Assignee: Shell Oil Company, Houston, Tex.

[21] Appl. No.: 675,034

[22] Filed: Apr. 8, 1976

Related U.S. Application Data

[63] Continuation of Ser. No. 504,220, Sep. 9, 1974, abandoned.

[30] Foreign Application Priority Data

Oct. 26, 1973 [GB] United Kingdom ............... 49962/73

[51] Int. Cl.$^2$ .................... B01J 21/04; B01J 23/04; B01J 23/50
[52] U.S. Cl. .................... 252/463; 252/476; 260/348.34
[58] Field of Search ............... 252/463, 476; 260/438.5 R

[56] References Cited

U.S. PATENT DOCUMENTS

| 2,671,764 | 3/1954 | Sacken | 252/476 |
| 3,575,888 | 4/1971 | Long | 252/476 |

FOREIGN PATENT DOCUMENTS 793658 7/1973 Belgium .

*Primary Examiner*—W. J. Shine

[57] ABSTRACT

When supported silver materials are being prepared, deposits of ionic, higher alkali metals, i.e., ionic potassium, rubidium, cesium or combinations thereof on porous supports with surface areas ranging from 0.1 to 7 square meters per gram prior to the deposit of silver improves the selectivity of these materials as catalysts for ethylene oxide. Optimal concentrations of the ionic, higher alkali metals are directly proportional to the surface area of the support.

10 Claims, No Drawings

PROCESS FOR PREPARING AN ETHYLENE OXIDE CATALYST

This is a continuation of application Ser. No. 504,220, filed Sept. 9, 1974, now abandoned.

BACKGROUND OF THE INVENTION

1. Field of the Invention

This invention relates to improved silver catalysts for the production of ethylene oxide, their preparation, and their use in ethylene oxide processes.

2. The Prior Art

Materials consisting of silver upon a support are known to be useful catalysts for the production of ethylene oxide by the controlled incomplete oxidation of ethylene with molecular oxygen. A great variety of modifications have been proposed to improve the activity and selectivity of these catalysts. These modifications have involved, for example, the supports employed, the method of production, the physical form of the silver on the support and the addition of additives to the catalyst.

The alkali metals and their salts have been repeatedly proposed as additives for various silver ethylene oxide catalysts. Carter, in U.S. Pat. No. 2,125,333, issued Aug. 2, 1938, was among the first to disclose alkali metal addition. He specified the use of "small amounts" of alkali metals, including both sodium or potassium, in his silver catalyst. Later patents elaborated on this disclosure, but often with contradictory teachings. McNamee et al in U.S. Pat. No. 2,238,474, issued Apr. 15, 1941, disclosed that while addition of 100 ppm by weight to 24% by weight of sodium improved silver catalysts, these amounts of potassium had a detrimental effect on catalyst performance. Sears, Jr. et al in U.S. Pat. No. 2,615,900, issued Oct. 28, 1952, cited a large number of promoters useful in broad weight ranges, but made no distinction in the effectiveness of the various promoters. Saken, in U.S. Pat. No. 2,671,764, issued Mar. 9, 1954 disclosed the use of large amounts of alkali metal sulfates. Saken in U.S. Pat. No. 2,765,283, issued Oct. 2, 1956, proposed adding from 1 ppm by weight to 2000 ppm by weight of an inorganic chlorine compound to the catalyst support. Saken's inorganic chlorine compounds included the alkali metal salts of chlorine acids, especially sodium chloride. Carlson et al in U.S. Pat. No. 2,773,844, issued Dec. 11, 1956, disclosed a multi-step silver deposition process for producing supported silver catalyst. Gould et al, in U.S. Pat. No. 2,799,687, issued July 16, 1957, disclosed that when from about 20 ppm by weight to about 1.6% by weight of inorganic halide (sodium chloride or preferably potassium chloride) are added as separate solid particles to a fluidized bed of supported silver catalyst, the halide acts as suppressant, inhibiting the catalyst activity. Hosoda et al in U.S. Pat. No. 3,144,416, issued Aug. 11, 1964, cited a number of promoter materials, but gave no critical limitations on their concentration. Kriger et al in U.S. Pat. No. 3,563,913 issued Feb. 16, 1971, generally disclosed the use of alkali and alkaline earth metals as promoters, listing specifically lithium with no reference to cesium, rubidium or potassium. He noted that these promoters are preferably added to the catalyst support before the latter is impregnated with the silver compound containing solution. Long in U.S. Pat. No. 3,575,888, issued Apr. 20, 1971, disclosed the use of aluminum oxide supports having a pore volume between about 0.15 and 0.30 $m^2/gm$ and surface area below about 10 $m^2/gm$. Nielson in U.S. Pat. No. 3,702,259, issued Nov. 7, 1972 used certain organic amine solubilizing/reducing agents to product uniformly spaced, adherent, hemispherical deposits of metallic silver on catalyst supports. Nielsen et al in Belgium Pat. No. 793,658, issued July 4, 1973, disclosed critical ranges for alkali metal additions simultaneously deposited with the silver on the catalyst support, but did not disclose any critical relationship between support surface area and alkali metal concentration. Nielsen further stated that the addition of the alkali prior to the addition of the silver offered little or no benefit.

The prior art clearly recognizes that alkali metal compound addition changes, for better or worse, the character of a silver ethylene oxide catalyst. There is no recognition, however, that the deposition of potassium, rubidium and cesium prior to the deposition of the silver in critical amounts proportional to the support surface area produces superior ethylene oxide catalyst.

STATEMENT OF THE INVENTION

It has now been found that certain materials consisting essentially of silver deposited on a refractory support exhibit improved selectivity as catalysts for the partial oxidation of ethylene to ethylene oxide. These materials are formed when ions of one or more of the alkali metals of atomic number 19 through 55 inclusive, that is, the alkali metals potassium, rubidium and cesium, are deposited on a catalyst support having a surface area ranging from about 0.1 to about 7 $m^2/g$ prior to the deposition of silver. The alkali metal concentrations for this invention are found to be directly proportional to the surface area of the support, the optimum concentration being 5±4 milligram equivalent weights per kilogram total catalyst for each square meter of surface area per gram of catalyst support. Operable alkali metal concentrations range from about 25 percent to about 175 percent of the optimum concentration. In contrast, it has been found that ions of the lower alkali metals, lithium and sodium, fail to cause commercially significant improvement at these levels.

DETAILED DESCRIPTION OF THE INVENTION

The Catalyst of the Invention

When supported silver catalyst materials are prepared by the deposition of potassium, rubidium, cesium or mixtures thereof on the support material with surface areas ranging from about 0.1 to about 7 square meters per gram prior to the deposition of the silver, a catalyst superior in selectivity for ethylene oxide production is produced.

Catalysts in accord with this invention comprise a porous refractory support having deposited on its exterior and interior (pore) surfaces from about 2% to about 20% by weight, based on total catalyst, of silver and certain amounts of ionic alkali metals. Of the common alkali metals, i.e., lithium, sodium, potassium, rubidium and cesium, only those alkali metals of atomic number from 19 through 55 inclusive, i.e., potassium, rubidium and cesium, are suitable. These three suitable metals will hereinafter be referred to as "the higher alkali metals". Excellent results are achieved with each of the three higher alkali metals. Potassium offers cost advantages, while cesium gives the greatest catalyst improvement. Mixtures of the higher alkali metals are also useful.

The higher alkali metals are present on the catalysts in the form of their cations, rather than as the extremely active free alkali metals. Silver, on the other hand, is present on the finished catalysts as silver metal.

The amount of the higher alkali metal (or metals) present on the catalyst surface is a critical function of the surface area. The concentrations of higher alkali metals of this invention are found to be directly proportional to the surface area of the support with the optimum concentration being preferably about 5±4 and more preferably 5±3 milligram equivalent weight per kilogram total catalyst for each square meter of surface area per gram of catalyst support ((mgew/kg)/(m$^2$/gm)). In other words, the optimum higher alkali metal concentration divided by the surface area is approximately a constant value. In this invention it is found that as the alkali metal concentration is increased from zero, the selectivity of the catalyst increases to a maximum, and at concentrations beyond the maximum the selectivity decreases again. The concentration at which this maximum in the selectivity occurs is referred to herein as the optimum alkali metal concentration. Further, since the approach to the optimum selectivity is gradual rather than a step function, there are alkali metal concentrations both above and below the optimum that also produce commercially significant improvements in catalyst selectivity and are considered within the scope of this invention. Hence, the alkali metal concentrations of the invention preferably include concentrations that range from about 25% to about 175% of the optimum concentration, more preferably from about 25% to about 150%, and most preferably from about 50% to about 150%. Expressed as the operable range, the higher alkali metal concentrations, relative to the support surface area range from about 0.25 to about 16, preferably from about 0.25 to about 14 and most preferably from about 0.5 to about 14 milligram equivalent weights per kilogram total catalyst for each square meter of surface area per gram of catalyst support (mgew/kg)/(m$^2$/gm). There appears to be minor variations in the concentration range of each of the higher alkali metals of this invention wherein optimum selectivity is obtained when the catalysts of this invention are employed in the partial oxidation of ethylene to ethylene oxide. It is thought, however, that these minor differences are attributable to undetermined experimental differences or other unknown variables, but they are not considered to be significant. While the optimum alkali metal concentration is directly proportional to the surface area of the catalyst support, not all surface areas provide commercially useful catalysts. The catalyst surface areas that have been found critical for this invention range from about 0.03 to about 10 square meters per gram (m$^2$/g).

It must be made clear that the amounts of potassium, rubidium and/or cesium deposited are not necessarily the total amounts of these metals present in the catalysts. They are the amounts of these alkali metals which are present on the surface of the catalyst and which are intentionally added to the catalysts prior to the addition of silver. It is not unusual for substantial amounts, often up to about 10,000 ppm wt. of these alkali metal (usually potassium) to be present within the porous support due to use of support materials containing naturally occurring alkali metals or inadvertent alkali metal addition during support manufacture. These amounts of alkali metal present in the support in non-leachable form do not appear to contribute to the improved performance of catalysts in accord with this invention and are neglected in determination of alkali metal concentrations. However, amounts of alkali metal present in the support in leachable form must be taken into account in determining the amounts of higher alkali metal deposited on the support. In fact, an alternate method of providing all or part of the desired amounts of the higher alkali metal is to incorporate the higher alkali metal in the support in leachable form during the manufacture of the support.

Catalysts according to this invention preferably contain from about 1% to about 25% by weight based on the total catalyst of silver as silver metal. Preferably they contain from about 2 to about 20 percent and most preferably from about 4% to about 16% by weight of silver. The use of larger amounts of silver is not excluded but is generally economically unattractive. The silver is deposited over the interior and exterior surfaces of the catalyst support and should be evenly dispersed over these surfaces.

The exact physical form of the silver upon the support can vary and does not appear to be critical to the invention. Very excellent results are obtained with the controlled surface alkali metal content catalyst of this invention, however, when the silver is present in the form of uniformly spaced, discontinuous, adherent, discrete particles having a uniform diameter of less than one micron (10,000 Å). Best results are obtained with this type of catalyst when the silver particles have diameters of from about 1000 to about 10,000 Å and most preferred catalysts have silver particles of an average diameter in the range of from about 1500 to about 7500 Å.

The support employed in these catalysts in its broadest aspects is selected from the large number of conventional, porous, refractory catalyst carriers or support materials which are essentially inert in the presence of the ethylene oxidation feeds, products and reaction conditions. Such conventional materials may be of natural or synthetic origin and preferably are of a macroporous structure, that is, a structure having a surface area below about 10 m$^2$/g and preferably below about 7 m$^2$/g. These support materials typically have an apparent porosity of greater than 20%. Very suitable supports comprise those of siliceous and/or aluminous composition. Specific examples of suitable supports are the aluminum oxides (including the materials sold under the trade name "Alundum"), charcoal, pumice, magnesia, zirconia, kieselguhr, fuller's earth, silicon carbide, porous agglomerates comprising silicon and/or silicon carbide, silica, magnesia, selected clays, artificial and natural zeolites and ceramics. Refractory supports particularly useful in preparation of catalysts in accordance with this invention comprise the aluminous materials, in particular those containing alpha alumina. In the case of alpha alumina-containing supports, preference is given to those having a specific surface area as measured by the B.E.T. method of from about 0.03 m$^2$/g to about 10 m$^2$/g and an apparent porosity as measured by conventional mercury or water absorption techniques of from about 10% to about 50% by volume. The B.E.T. method for determining specific surface area is described in detail in Brunauer, S., Emmet, P. H., and Teller, E., *J. Am. Chem. Soc.*, 60, 309-16 (1938).

When certain types of alpha alumina-containing supports are employed, the advantages of the special alkali metal addition of this invention are especially emphasized. These alpha alumina supports have relatively uniform pore diameters and are more fully characterized by having (1) B.E.T. specific surface areas of from about 0.03 m²/g to about 10 m²/g, preferably about 0.1 m²/g to about 7 m²/g.

Regardless of the character of the support used, it is preferably shaped into particles, chunks, pieces, pellets, rings, spheres, and the like of a size suitable for employment in fixed bed applications. Conventional commercial fixed bed ethylene oxidation reactors are typically in the form of a plurality of parallel elongated tubes (in a suitable shell) approximately 1 to 2 inches in diameter and 24 to 45 feet long filled with catalyst. In such reactors, it is desirable to employ a support formed into a rounded shape, such as for example, spheres, pellets, rings, tablets, and the like, having diameters of from about 0.1 inch to about 0.8 inch.

The Catalyst Preparation

The catalysts of the invention are prepared by a technique in which the desired alkali metal is deposited on the catalyst support surface prior to the deposition of the silver.

In general terms, catalysts in accord with this invention are prepared by (A) contacting a suitable solid porous refractory support with a liquid phase which contains a suitable amount of dissolved potassium, rubidium and/or cesium salts, (B) at least partially drying this impregnated support, and (C) recontacting the alkali metal impregnated support with a liquid phase which contains an amount of silver, either as silver compounds dissolved in the liquid phase or as a slurry of silver particles in an amount sufficient to deposit from 1 to 25% by weight of silver on the support surface and (D) thermally treating the resulting product as is necessary in the presence of a reducing agent to convert the silver compound to silver metal. The exact concentrations of alkali metal salts and silver compounds employed in the impregnating solution may generally require some routine experimentation since the amount of alkali metal salts and silver compounds deposited will depend in part in the porosity and surface area of the catalyst support. However, methods of varying the amount of alkali metal and silver deposited are conventional, as is the analytical determination of the amount of the materials actually present.

Preferably the impregnating liquid in step A above contains the salt of the higher alkali metal in such concentration as to produce in the final product a higher alkali metal concentration from about 0.25 to about 16 and more preferable from about 0.25 to about 14 and most preferably from about 0.50 to about 14 milligram equivalent weights per kilogram total catalyst for each square meter of support surface area.

Also within the scope of the invention is an alternative method of depositing the higher alkali metal salt on the support surface which provides a ready means of controlling the amount of higher alkali metal deposited within the limits of the invention. This method involves deposition of larger then required amounts of the higher alkali metal salts according to step (A) in the general procedure described above followed by contacting the catalyst particles so obtained after either step (B) or step (D) of the procedure described above with a suitable solvent, for example an anhydrous alkanol of 1 or 2 carbon atoms, methyl or ethyl acetate, tetrahydrofuran, etc. The higher alkali metals contemplated by this invention are soluble in the solvents described to a sufficient degree that one or more washings with these solvents will selectively remove the excess higher alkali metal such that the amount remaining intact on the support surface falls within the concentration range critical to the invention. This method then provides a ready means of adjusting the higher alkali metal concentration from levels in excess of those described by the invention, whether the result of purposeful or inadvertent actions, to specific concentrations within the limits of the invention, by a process which is readily applicable to large plant scale operations.

An excellent method for adding the desired alkali metals is to dissolve them as suitable salts in an aqueous phase in an amount regulated to give the required alkali metal addition to the finished catalyst when the support is contacted therewith. Suitable higher alkali metal salts generally include all those which are soluble in an aqueous phase. In this regard, no unusual effectiveness is observed with use of any particular anion in the alkali metal salts. For example, hydroxide, nitrates, nitrites, chlorides, iodides, bromates, bicarbonates, oxalates, acetates, tartrates, lactates, isopropoxides, and similar common alkali metal salts may be used. The support after impregnation with the higher alkali metal is dried in any suitable manner, for example, by increasing the temperature to a value between about 100° C. to 200° C. for a time from about 0.1 to about 8 hours with multiple temperatures being suitable and conducting an inert gas over the heated support. Suitable inert gases are nitrogen, air, hydrogen, noble gases, carbon dioxide, methane and mixtures of these gases. Drying can be performed at atmospheric, sub-, and super atmospheric pressures. Vacuum and freeze-drying are also suitably employed.

A great variety of methods for adding silver to supports are known. In a typical method, the support may be impregnated with an aqueous solution of silver nitrate, dried, and the silver reduced with hydrogen or hydrazine as described in U.S. Pat. No. 3,575,888, issued Apr. 20, 1971, to Long. In another technique the support may be impregnated with an ammoniacal solution of silver oxalate or carbonate and the silver metal formed by thermally decomposing the salt. Silver may be added as well by the technique disclosed in U.S. Pat. No. 3,702,259 of Nielsen, wherein the support is impregnated with special aqueous solutions of silver salts and combinations of ammonia, vicinal alkanolamines and/or vicinal alkyldiamines and then thermally treated. Other possible methods for adding silver include impregnating a support with an ethanolamine-containing solution of silver salt and then reducing, as disclosed by Japanese Patent No. 19606/1971, or by adding a slurry of fine particles of silver carbonate to the support and thermally decomposing as described by Endler in U.S. Pat. No. 3,043,854 issued July 10, 1962, or adding silver in the form of "cluster" silver as by the process described by Bryce-Smith in U.S. Pat. No. 3,781,317, issued Dec. 25, 1973. In each of these techniques, silver is added to the support when the support is contacted with a liquid phase containing either a silver solution or a slurry of silver particles.

A particularly effective method of depositing the silver is where the silver is added to the support from a basic solution, particularly from a nitrogenous base-containing basic solution. Examples of these nitrogenous bases are ammonia, the alkylamines and the alkanolamines.

Thus, in a preferred embodiment, catalysts of this invention are prepared by (A) impregnating a porous aluminous support with an aqueous solution of the appropriate alkali metal salt, (B) drying the impregnated support in a stream of nitrogen at 100° C. to 200° C. for 0.1 to 4 hours, (C) contacting the dried, impregnated support with a solution of silver salts and (D) maintaining the product of (C) at a temperature of from about 100° C. to about 500° C., optionally in the presence of a reducing agent, for a period of time sufficient to convert the silver salt to silver metal.

In a particularly preferred modification the silver addition to the catalyst support is made by techniques such as those disclosed in U.S. Pat. No. 3,702,259 of Nielsen. This preferred preparation method involves impregnation of an alumina support with certain aqueous alkali metal silver salt solutions and a subsequent thermal reduction of the silver salt. The silver impregnation solution consists essentially of:

A. a silver salt of a carboxylic acid,
B. an organic amine alkaline solubilizing/reducing agent, and
C. and additional aqueous solvent as is required to achieve the desired silver level Suitable carboxylic acid silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution used in this preparation method. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are preferred. They are the following:

A. vicinal alkylenediamines of from 2 to 4 carbon atoms;
B. mixtures of (1) vicinal alkanolamines of from 2 to 4 carbon atoms and (2) vicinal alkylenediamines of from 2 to 4 carbon atoms;
C. mixtures of vicinal alkylenediamines of from 2 to 4 carbon atoms and ammonia; and
D. mixtures of vicinal alkanolamines of from 2 to 4 carbon atoms and ammonia.

These preferred solubilizing/reducing agents are generally added in the amount of from 0.1 to 10 moles per mole of silver present.

Very preferred as solubilizing/reducing agents are:
A. ethylenediamine,
B. ethylenediamine in combination with ethanolamine,
C. ethylenediamine in combination with ammonia and
D. ethanolamine in combination with ammonia.

Ethylenediamine, alone or in combination with ethanolamine, is most preferred.

When ethylenediamine is used as the sole solubilizing/reducing agent, it is necessary to add amounts of the amine in the range of from 0.1 to 5.0 moles of ethylenediamine per mole of silver.

When ethylenediamine and ethanolamine together are used as solubilizing/reducing agent, it is suitable to employ from 0.1 to 3.0 moles of ethylenediamine per mole of silver and from 0.1 to 2.0 moles of thanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

As already noted, it is essential that only certain controlled amounts of the higher alkali metals of the invention be present, these amounts being a function of the surface area of the catalyst support. These amounts are achieved by either controlled addition of alkali metal to the support in the first impregnation step or by controlled removal of excess alkali metal from the impregnated catalyst support either before or after the silver impregnation step.

Subsequent to the use of any of these methods, the impregnated support is then heated at a temperature of from 100° to 375°, preferably from 125° to 325° C., for the time, typically 0.1 to 8 hours, required to decompose the silver salt and form the adherent particulate deposit of metallic silver on the surfaces. Lower temperatures do not adequately decompose the silver salt and should be avoided. More than one temperature may be employed.

Ethylene Oxide Production

The higher alkali metal-promoted silver catalysts have been shown to be particularly selective catalysts in the direct oxidation of ethylene with molecular oxygen to ethylene oxide. The conditions for carrying out such an oxidation reaction in the presence of the silver catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Pressures in the range of from about atmospheric to about 500 psi are generally employed. Higher pressures may, however, be employed within the scope of the invention. Molecular oxygen employed as reactant is obtained from conventional sources. The suitable oxygen charge may consist essentially of relatively pure oxygen, a concentrated oxygen stream comprising oxygen in major amounts with lesser amounts of one or more diluents such as nitrogen, argon, etc., or another oxygen-containing stream such as air. The use of the present novel silver catalysts in ethylene oxidation reactions is in no way limited to the use of specific conditions among those which are known to be effective.

In a preferred application of the silver catalysts of the invention ethylene oxide is produced when an oxygen-containing gas of not less than 95% oxygen is contacted with ethylene in the presence of the present catalysts at a temperature in the range of from 210° C. to 285° C. and preferably 225° C. to 270° C.

The resulting ethylene oxide is separated and recovered from the reaction products by conventional methods known and used in the art. Use of the silver catalysts of the invention in ethylene oxide production processes gives higher overall ethylene oxidation selectivities to ethylene oxide at a given ethylene conversion than is possible with conventional catalysts.

While the reason for these higher selectivities observed with catalysts of this invention is not fully understood, experiments have indicated that conventional silver catalysts (not containing higher alkali metals) cause ethylene oxide to combust after formation while silver catalysts containing higher alkali metals according to this invention do not cause as extensive ethylene oxide combustion.

Preparation of catalysts according to the invention and their use in the production of ethylene oxide will be further described by the following examples which are provided for illustration and are not to be construed as limiting the invention.

ILLUSTRATIVE EMBODIMENT I

A series of catalysts were prepared using alumina supports with different surface areas. The physical properties of these supports are shown in Table I.

TABLE I

| Catalyst Support | A | B | C | D | E |
|---|---|---|---|---|---|
| Surface area, m²/g | 0.19 | 0.51 | 1.07 | 1.32 | 6.55 |
| Form of particles | rings 8 mm | spheres, diam. 5 mm | cylinders, diam. 5mm | rings, diam. 15 mm | spheres, diam. 2.5 mm |
| Sodium content, %w | 0.02 | 0.13 | 0.24 | 0.40 | 0.52 |
| Zinc content, %w | — | — | 0.24 | 0.23 | — |
| Silica content, %w | 0.26 | 2.37 | 0.15 | 0.28 | 2.5 |
| Iron content, %w | 0.09 | 0.45 | 0.04 | 0.03 | 0.05 |
| Trace metals other than Na, Zn, Si and Fe, %w oxides | 0.33 | 0.85 | 0.25 | 0.3 | 0.3 |
| Apparent porosity ('), %v | 24 | 50 | 25 | 25 | 40 |
| Median pore diameter, micron | 3.9 | 2 | 0.8 | 0.6 | 0.25 |
| 80% of the pores had diameters in the range of from .. to .. micron | 1.5–15 | 0.3–10 | 0.4–1.2 | 0.2–1.5 | 0.1–0 |
| Pore volume (''), ml/g | 0.23 | | 0.25 | 0.22 | 0.45 |

(') from water absorption.
('') determined by means of mercury porosimeter.

Catalysts designated A-1, A-2, . . . , B-1, etc. were made in accord with this invention, that is, by the sequential deposition of the alkali metal and the silver. Catalysts designated NA-0, NB-0, . . . , NI-0, etc. were not in accord with the invention in that they contained no alkali metal. Catalysts designated NA-1, NA-2, . . . , NB-1, etc. were also not in accord with this invention in that the deposition of the alkali metal and the silver were made simultaneously.

To illustrate the preparation of catalysts in accord with this invention the preparation of catalysts made with support B is set out below. The other catalysts in accord with the invention were prepared in a similar fashion.

30 Grams of support B having a surface area of 1.07 m²/g were first impregnated under a pressure 0.04 bar absolute in a rotary evaporator with 8.5 ml of an aqueous solution containing 3 mg cesium hydroxide per ml solution. The impregnated support was dried by heating for 30 min at 110° C. and then for two hours at 150° C. in a stream of nitrogen.

The support was then impregnated with an aqueous solution of silver salt. This solution was prepared by the following technique. 6 Grams anhydrous silver nitrate and 3.3 grams potassium oxalate (K₂C₂O₄.1 H₂O) were separately dissolved in quantities of 100 ml of water. The solutions obtained were mixed and heated on a steam bath. The silver oxalate precipitate was centrifuged and the supernatant liquid decanted. Subsequently, the precipitate was washed five times with 100 ml hot (60°–90° C.) distilled water. The precipitate was centrifuged and the water decanted after each washing. The precipitate was then dissolved in 10 ml of a mixture consisting of 75% v of 1,2-diaminoethane and 25% v of water, the mixture being cooled in ice. A quantity of 30 grams of the cesium-containing support was then consecutively impregnated at a pressure of 0.04 bar abs. in a rotary evaporator, with 8.5 ml of the latter liquid, warmed up by indirect heat exchange with hot water to a temperature of 60° C. with rotation, again at 0.04 bar abs, to partially remove the solvent, poured out onto a large filter paper and gently shaken to remove any excess moisture, heated in a stream of air for a period of two minutes until a temperature of 250° C. was attained and kept at 250° C. for a further five minutes. The catalyst was then cooled to ambient temperature. The silver content of the catalyst was 7.8% by weight. The cesium content amounted to 3.35 mgew per kg catalyst. Examination of the catalyst with an electron microscope revealed that the silver had been deposited on the support as discrete particles with a uniform diameter of from 0.05 to 0.3 microns (500 to 3000 Å).. The silver particles were uniformly spaced over the surface of the support.

To prepare the NA-0, . . . , NE-0 series of catalysts which did not contain any alkali metal, the first impregnation step with the cesium hydroxide solution described above was omitted with the subsequent steps being substantially the same.

To prepare the NA-1, NA-2, . . . NB-5, series of catalysts in accord with the invention, the first impregnation step with the cesium hydroxide described above was also omitted. The subsequent steps were followed in a substantially similar fashion with the exception that cesium hydroxide was added to the silver-ethylenediamine-water solution in sufficient quantities to provide the desired alkali metal content in the final catalyst product.

The catalysts prepared above were comparatively tested for the production of ethylene oxide. The reactor consisted of a tube with an internal diameter of 5 mm and was in each experiment filled over a length of 12 cm. with catalyst particles whose dimensions were in the range between 0.4 and 0.8 mm. These catalyst particles were obtained by crushing the catalyst particles prepared as described in the above.

A mixture containing oxygen and ethylene was conducted through the catalyst bed in the presence of a small amount of vinyl chloride as a moderator under the following conditions:

| Pressure | 14.5 bar abs. |
| --- | --- |
| space velocity | 3300 h$^{-1}$ |
| ethylene in feed | 30% m |
| oxygen in feed | 8.5% m |
| nitrogen in feed | 61.5% m | moderator concentration, parts of vinyl chloride per million parts of feed (vol) 10 ppm The reaction temperature was adjusted to provide for an oxygen conversion of 52% and the selectivity to ethylene oxide was determined. The results of the above described experiments are shown in Tables A thru E. As can be noted from these tables, at the lowest support surface areas used, the sequential deposition method of this invention give similar results to the simultaneous deposition method. However, with the more desirable higher surface area supports, the technique of this invention produces far superior catalyst to those not produced in accord with this invention.

Table A:

Catalyst Prepared with Supports Having Surface Areas of 0.19 m$^2$/g

| Catalyst | Silver Content | Cesium Content | | Reactor Temp. to achieve 52% O$_2$ Conversion, °C. | Oxidation Selectivity to Ethylene Oxide, % |
| --- | --- | --- | --- | --- | --- |
| | | mgew/kg | ppm.wt. | | |
| A-1[1] | 7.0 | 0.86 | 114 | 259 | 79.9 |
| A-2 | 7.6 | 1.01 | 134 | 255 | 80.3 |
| A-3 | 7.9 | 1.11 | 148 | 259 | 80.7 |
| A-4 | 7.6 | 1.49 | 198 | 265 | 79.8 |
| A-5 | 8.2 | 1.65 | 220 | 261 | 79.0 |
| NA-0 | 7.8 | 0 | 0 | 251 | 69.5 |
| NA-1 | 8.3 | 0.77 | 103 | 254 | 80.3 |
| NA-2 | 8.3 | 1.08 | 143 | 258 | 80.6 |
| NA-3 | 7.7 | 1.25 | 166 | 263 | 80.2 |
| NA-4 | 7.8 | 1.64 | 218 | 264 | 79.7 |
| NA-5 | 8.0 | 1.89 | 252 | 295 | 76.1 |

[1]A-1, A-2, B-1, etc., are catalysts prepared according to this invention.
NA-0, NB-0, etc., are catalysts not according to this invention and with no alkali metal addition.
NA-1, NA-2, NB-1, etc., are catalysts not according to this invention and prepared by the simultaneous disposition of alkali metal with the silver.

Table B:

Catalyst Prepared with Supports Having Surface Areas of 0.51 m$^2$/g

| Catalyst | Silver Content | Cesium Content | | Reactor Temp. to achieve 52% O$_2$ Conversion, °C. | Oxidation Selectivity to Ethylene Oxide, % |
| --- | --- | --- | --- | --- | --- |
| | | mgew/kg | ppm.wt. | | |
| B-1* | 7.7 | 0.89 | 118 | 254 | 74.5 |
| B-2 | 7.9 | 1.53 | 204 | 252 | 77.8 |
| B-3 | 7.7 | 2.79 | 371 | 258 | 78.2 |
| B-4 | 7.5 | 3.77 | 502 | 259 | 76.5 |
| B-5 | 7.9 | 5.50 | 732 | >300 | 70.4 |
| NB-0 | 7.7 | 0 | 0 | 251 | 71.0 |
| NB-1 | 7.1 | 2.64 | 351 | 261 | 77.6 |
| NB-2 | 7.4 | 3.78 | 503 | 274 | 76.1 |
| NB-3 | 8.0 | 5.47 | 728 | >300 | 64 |

*See footnote 1 of Table A

Table C:

Catalyst Prepared with Supports Having Surface Areas of 1.07 m$^2$/g

| Catalyst | Silver Content | Cesium Content | | Reactor Temp. to achieve 52% O$_2$ Conversion, °C. | Oxidation Selectivity to Ethylene Oxide, % |
| --- | --- | --- | --- | --- | --- |
| | | mgew/kg | ppm.wt. | | |
| C-1* | 8.4 | 1.56 | 208 | 237 | 77.7 |
| C-2 | 8.8 | 3.52 | 468 | 249 | 78.4 |
| C-3 | 10.7 | 6.03 | 802 | 255 | 79.5 |
| C-4 | 8.7 | 6.59 | 877 | 256 | 77.5 |
| C-5 | 10.6 | 7.95 | 1058 | 268 | 76.4 |
| NC-0 | 8.0 | 0 | 0 | 260 | 71.9 |
| NC-1 | 8.0 | 1.87 | 249 | 251 | 75.1 |
| NC-2 | 8.0 | 3.11 | 430 | 260 | 75.9 |
| NC-3 | 8.4 | 4.08 | 543 | 252 | 76.2 |
| NC-4 | 9.2 | 4.80 | 639 | 257 | 74.7 |
| NC-5 | 8.0 | 5.43 | 722 | 320 | 67.8 |

*See footnote 1 of Table A

Table D:

Catalyst Prepared with Supports Having Surface Areas of 1.32 m$^2$/g

| Catalyst | Silver Content | Cesium Content | | Reactor Temp. to achieve 52% O$_2$ Conversion, °C. | Oxidation Selectivity to Ethylene Oxide, % |
| --- | --- | --- | --- | --- | --- |
| | | mgew/kg | ppm.wt. | | |
| D-1* | 6.6 | 4.19 | 557 | 260 | 67.0 |
| D-2 | 6.0 | 6.35 | 844 | 265 | 73.2 |
| D-3 | 6.9 | 7.69 | 1024 | 264 | 75.4 |
| D-4 | 7.2 | 9.56 | 1272 | 261 | 74.3 |
| ND-0 | 5.4 | 0 | 0 | 257 | 66.0 |
| ND-1 | 5.4 | 4.08 | 543 | 293 | 65.6 |
| ND-2 | 5.4 | 4.69 | 624 | 289 | 63.2 |

Table E:

Catalyst Prepared with Supports Having Surface Areas of 6.55 m$^2$/g

| Catalyst | Silver Content | Cesium Content | | Reactor Temp. to achieve 52% O$_2$ Conversion, °C. | Oxidation Selectivity to Ethylene Oxide, % |
| --- | --- | --- | --- | --- | --- |
| | | mgew/kg | ppm.wt. | | |
| E-1* | 11.5 | 25.7 | 3420 | 207 | 73.3 |
| E-2 | 11.0 | 35.3 | 4690 | 205 | 75.4 |
| E-3 | 11.2 | 39.5 | 5250 | 205 | 75.1 |
| NE-0 | 9.4 | 0 | 0 | 220 | 50.0 |
| NE-1 | 11.9 | 42.3 | 5621 | 277 | 42.4 |

*See footnote 1 of Table A

ILLUSTRATIVE EMBODIMENT II

Example 1

Catalysts in accord with this invention containing varying amounts of potassium as the higher alkali metal component were prepared using the feedstocks and general preparative techniques of Illustration Embodiment I. Instead of adding cesium to the first impregnating solution, potassium as potassium hydroxide was added. The catalyst compositions, so prepared, were tested as ethylene oxide catalysts using the apparatus and technique of Illustrative Embodiment I. The compositions of these catalysts along with the results are given in Table F below:

Table F:

Catalyst Prepared with Supports Having Surface Areas of 0.19 m²/g

| Catalyst | Silver Content | Potassium Content mgew/kg | ppm.wt. | Reactor Temp. to achieve 52% O₂ Conversion, °C. | Oxidation Selectivity to Ethylene Oxide, % |
|---|---|---|---|---|---|
| F-1* | 7.8 | 1.74 | 68 | 256 | 79.8 |
| NF-0 | 7.8 | 0 | 0 | 251 | 69.5 |

*See footnote 1 of Table A

Example 2

Catalysts in accord with this invention containing varying amounts of rubidium as the higher alkali metal component were prepared using the feedstocks and general preparative techniques of Illustrative Embodiment I. Instead of adding cesium hydroxide to the first impregnating solution, rubidium as rubidium hydroxide was added. The catalyst compositions, so prepared were tested as ethylene oxide catalyst using the apparatus and technique of Illustrative Embodiment I. The compositions of the catalysts along with the results are given in Table G below:

Table G:

Catalyst Prepared with Supports Having Surface Areas of 0.19 m²/g

| Catalyst | Silver Content | Rubidium Content mgew/kg | ppm.wt. | Reactor Temp. to achieve 52% O₂ Conversion, °C. | Oxidation Selectivity to Ethylene Oxide, % |
|---|---|---|---|---|---|
| G-1* | 7.8 | 1.06 | 90 | 252 | 76.7 |
| NG-0 | 7.8 | 0 | 0 | 251 | 69.5 |

*See footnote 1 of Table A

Example 3

Catalysts containing varying amounts of lithium, an alkali metal not falling within the scope of this invention, were prepared using the feedstocks and general preparative techniques of Illustrative Embodiment I. Instead of adding cesium hydroxide to the first impregnating solution, lithium as lithium hydroxide was added. The catalyst compositions so prepared were tested as ethylene oxide catalysts using the apparatus and technique of Illustrative Embodiment I. The composition of these catalysts along with the results are given in Table H Below:

Table H:

Lithium Catalyst prepared with Supports Having Surface Areas of 0.19 m²/g

| Catalyst | Silver Content | Lithium Content mgew/kg | ppm.wt. | Reactor Temp. to achieve 52% O₂ Conversion, °C. | Oxidation Selectivity to Ethylene Oxide, % |
|---|---|---|---|---|---|
| NH-0* | 7.8 | 0 | 0 | 251 | 69.5 |
| NH-1 | 6.9 | 28 | 200 | 250 | 73.5 |
| NH-2 | 6.9 | 56 | 390 | 250 | 72.4 |
| NH-3 | 6.9 | 72 | 500 | 252 | 72.8 |

*See footnote 1 of Table A

Example 4

Catalysts containing varying amounts of sodium, an alkali metal not falling within the scope of this invention were prepared using the feedstocks and general preparative techniques of Illustrative Embodiment I. Instead of adding cesium hydroxide to the first impregnating solution, sodium as sodium hydroxide was added. The catalyst compositions so prepared were tested as ethylene oxide catalysts using the apparatus techniques of Illustrative Embodiment I. The composition of these catalysts along with the results are given in Table I below:

Table I:

Sodium Catalyst Prepared with Supports Having Surface Areas of 0.19 m²/g

| Catalyst | Silver Content | Sodium Content mgew/kg | ppm.wt. | Reactor Temp. to achieve 52% O₂ Conversion, °C. | Oxidation Selectivity to Ethylene Oxide, % |
|---|---|---|---|---|---|
| NI-0 | 7.8 | 0 | 0 | 251 | 69.5 |
| NI-1 | 7.1 | 1.22 | 28 | 252 | 72.3 |
| NI-2 | 7.1 | 2.17 | 50 | 251 | 74.1 |
| NI-3 | 7.1 | 3.22 | 74 | 249 | 75.7 |
| NI-4 | 7.1 | 3.57 | 82 | 254 | 75.5 |
| NI-5 | 7.1 | 4.39 | 101 | 254 | 75.5 |

What is claimed is:

1. A process for preparing a catalyst article for the production of ethylene oxide which comprises;
    (a) impregnating a porous refractory support having a surface area from about 0.03 m²/g to about 10 m²/g with an aqueous solution of a salt of a higher alkali metal selected from the group consisting of potassium, rubidium, cesium or mixtures thereof in such concentration as to produce in the final product a higher alkali metal concentration from about 0.25 to about 16 milligram equivalent weights per kilogram total catalyst for each square meter of support surface area ((mgew/kg)/(m²/g));
    (b) at least partially drying the product of step (a) at a temperature between about 100° C. and about 200° C. sufficiently to allow the impregnation of step (c);
    (c) recontacting the higher alkali metal impregnated support with a liquid phase containing dissolved therein a silver compound in an amount sufficient to deposit from about 1 to about 25 percent by weight of silver on the support surface, and
    (d) thermally treating the resulting product in the presence of a reducing agent to convert the silver compound to silver metal.

2. The process in accord with claim 1 wherein the higher alkali metal is potassium.

3. The process in accord with claim 1 wherein the higher alkali metal is rubidium.

4. The process in accord with claim 1 wherein the higher alkali metal is cesium.

5. The process in accord with claim 1 wherein the higher alkali metal concentration in the final product ranges from about 0.25 to about 14 (mgew/kg)/(m²/g).

6. The process in accord with claim 1 wherein the higher alkali metal concentration in the final product ranges from about 0.5 to about 14 (mgew/kg)/(m²/g).

7. The process in accord with claim 5 wherein the silver deposited ranges from about 2 to about 20 percent by weight.

8. The process in accord with claim 6 wherein the silver deposited ranges from about 4 to about 16 percent by weight.

9. The process in accord with claim 1 wherein the porous refractory support comprises alpha alumina.

10. The process in accord with claim 9 wherein the surface area of the support ranges from about 0.1 to about 7 m²/g.